United States Patent [19]

Redmond et al.

[11] Patent Number: 5,431,899
[45] Date of Patent: Jul. 11, 1995

[54] ROTAVIRUS VP6 AS A DIAGNOSTIC AND TARGETING AGENT

[75] Inventors: Mark J. Redmond; Manuel Campos; Gilbert G. Matte; Deborah M. Haines, all of Saskatoon, Canada

[73] Assignee: University of Saskatchewan, Saskatchewan, Canada

[21] Appl. No.: 650,041

[22] Filed: Feb. 4, 1991

[51] Int. Cl.6 .................. A61K 51/12; C12Q 1/70; G01N 33/566; C07K 14/14

[52] U.S. Cl. ........................... 424/1.57; 435/5; 435/7.24; 435/235.1; 436/501; 436/519; 530/350; 530/826

[58] Field of Search ............ 436/501, 5, 519; 435/235.1; 530/350, 826; 424/1.57

[56] References Cited

U.S. PATENT DOCUMENTS

| | | |
|---|---|---|
| 4,642,232 | 2/1987 | Yman . |
| 5,071,651 | 12/1991 | Sabara et al. . |
| 5,087,616 | 2/1992 | Myers et al. ................. 514/21 |
| 5,102,990 | 4/1992 | Rhodes . |
| 5,298,244 | 3/1994 | Redmond et al. ............... 424/89 |

OTHER PUBLICATIONS

Embleton et al., "Antibody Targeting of Anti-Cancer Agents," in *Monoclonal Antibodies for Cancer Detection and Therapy* (Academic Press, London) Chapter 16: 317–344 (1985).
Estes et al., *Nucleic Acids Res.* (1984) 12:1875–1887.
Estes et al., *J. Virol.* (1987) 61:1488–1494.
Yeager et al., *J. Cell Biol.* (1990) 110:2133–2144.

*Primary Examiner*—Michael P. Woodward
*Attorney, Agent, or Firm*—Morrison & Foerster

[57] ABSTRACT

Advantage is taken of the ability of rotaviral VP6 protein to home to macrophage and monocytes to provide label to these cells in either an in vitro or in vivo environment. Further, the ability to couple label to the VP6 protein and to couple VP6 to a targeting agent provides a mechanism for conducting label (or an effector moiety) to any desired target.

9 Claims, 2 Drawing Sheets

ROTAVIRUS VP6 AS A DIAGNOSTIC AND TARGETING AGENT

TECHNICAL FIELD

The invention relates to in vivo diagnosis and labeling of specific tissues, as well as targeted drug delivery. More specifically, the invention concerns use of rotaviral VP6 protein in these applications.

BACKGROUND ART

The inner capsid protein of rotavirus, designated VP6 and having a molecular weight of approximately 45 kd, has been disclosed as an immunogen for use in vaccines to prevent rotaviral infection and also, more importantly, as a carrier for an immunogenic complex generally. U.S. Pat. No. 5,071,651 filed 2 Mar. 1990 which is a file-wrapper continuation of U.S. Ser. No. 092,120 filed 2 Sep. 1987, describes in detail the advantageous properties of the VP6 rotaviral protein as an immunological carrier. The contents of the specification are incorporated herein by reference.

As described in the above specification, VP6 is the most abundant structural protein in rotavirus and has an approximate molecular weight of 45 kd. The gene encoding this protein has been cloned and the protein has been produced by recombinant methods (Estes et al., *Nucleic Acids Res* (1984) 12:1875–1887; Estes et al., *J Virol* (1987) 61:1488–1494). The complete amino acid sequences as well as the sequences of the VP6-encoding DNA is known for at least nine strains of rotavirus.

The above-referenced application describes methods for the recombinant production of the VP6 protein and describes its structural characteristics. Of interest herein, VP6 protein is known to aggregate into tubular particles under conditions from about pH 5-pH 9, which particles are moderately stable to changes in temperature and ionic strength. Spherical particles resembling single-shelled virus can be formed at about pH 4 and are now known to be approximately $2 \times 10^{-22}$ meters$^3$ in volume with a diameter of about 70 nm. The surface of the sphere appears to be perforated by 132 channels which are 40–60 angstroms in diameter (Yaeger, et al. *J Cell Biol* (1990) 110:2133–2144). A copending application Ser. No. 07/650,054 filed on even date herewith, describes encapsulation of various biological effector molecules in these spheres. In addition, the VP6 protein can be made to form sheets composed of a small-holed lattice in samples where the solutions have been shifted from about pH 6 to about pH 4.

As described in the above-referenced U.S. Pat. No. 5,071,651, VP6 protein acts as a carrier useful in immunogenic complexes to provoke immunogenic responses to haptens or antigens coupled to the surface of the carrier. The hapten or antigen may be coupled to the carrier using standard conventional coupling techniques, including coupling of polypeptide or protein haptens or antigens to the carrier by synthesis of a fusion protein combining the VP6 with the antigen. Other methods include, for example, coupling of carbohydrates using reductive amination techniques and coupling of carbohydrates or other proteins using linkers such as those available from Pierce Chemical Company, Rockford, Ill.. Unique to VP6, however, is its ability to interact with a "binding peptide" through protein-protein interaction, provided the binding peptide has a region of appropriate sequence, as explained in the referenced application. The binding peptide can be used to mediate binding of antigen or hapten to the VP6 carrier by coupling the antigen or hapten to the binding peptide and then binding to VP6 through protein-protein interaction.

While the use of VP6 as an immunological carrier is clearly disclosed in the above-referenced application, there is no suggestion or realization that VP6 particles are useful to mediate diagnosis by virtue of their ability, described herein, to home specifically to macrophages and monocytes. In addition, there is no suggestion that the VP6 carrier, by virtue of its ease of interaction with specific targeting agents can be used to effect targeted drug delivery or localization of label to additional targets.

DISCLOSURE OF THE INVENTION

The invention results in part from the discovery that VP6 aggregates home to macrophages and monocytes in vivo and in vitro, and that therefore VP6 can directly be used as a carrier to deliver diagnostic reagents to these cells. It has further been found that by taking advantage of the ability of VP6 to bind easily to specific targeting agents, diagnostic labels and drugs can be effectively delivered to arbitrarily selected target cells or tissues.

Thus, in one aspect, the invention is directed to compositions and methods which specifically deliver label to macrophages or monocytes in vivo or in vitro using VP6 as a homing reagent. In another aspect, the invention is directed to methods and materials useful in targeting tissues or cells utilizing a targeting agent coupled to VP6, which VP6 is, in turn, coupled to the biologically effective substance to be delivered.

MODES OF CARRYING OUT THE INVENTION

Figure 1:
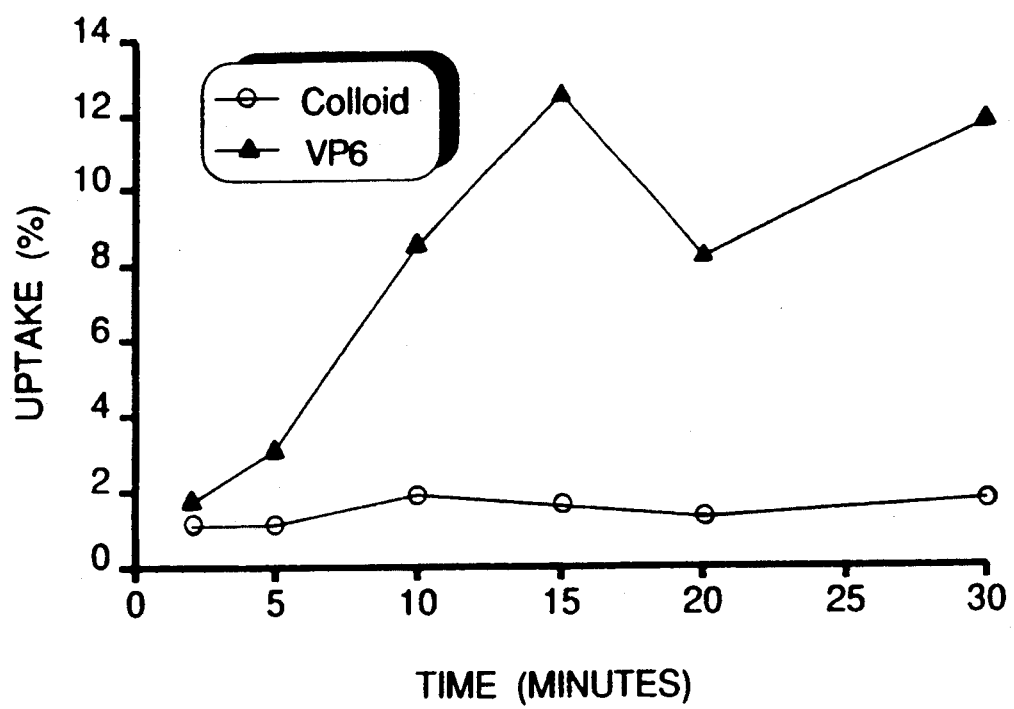
FIG. 1 shows the in vitro uptake of $^{99M}$technetium labeled VP6 by alveolar macrophages in comparison to colloidal particles of the same dimension.
Figure 2:
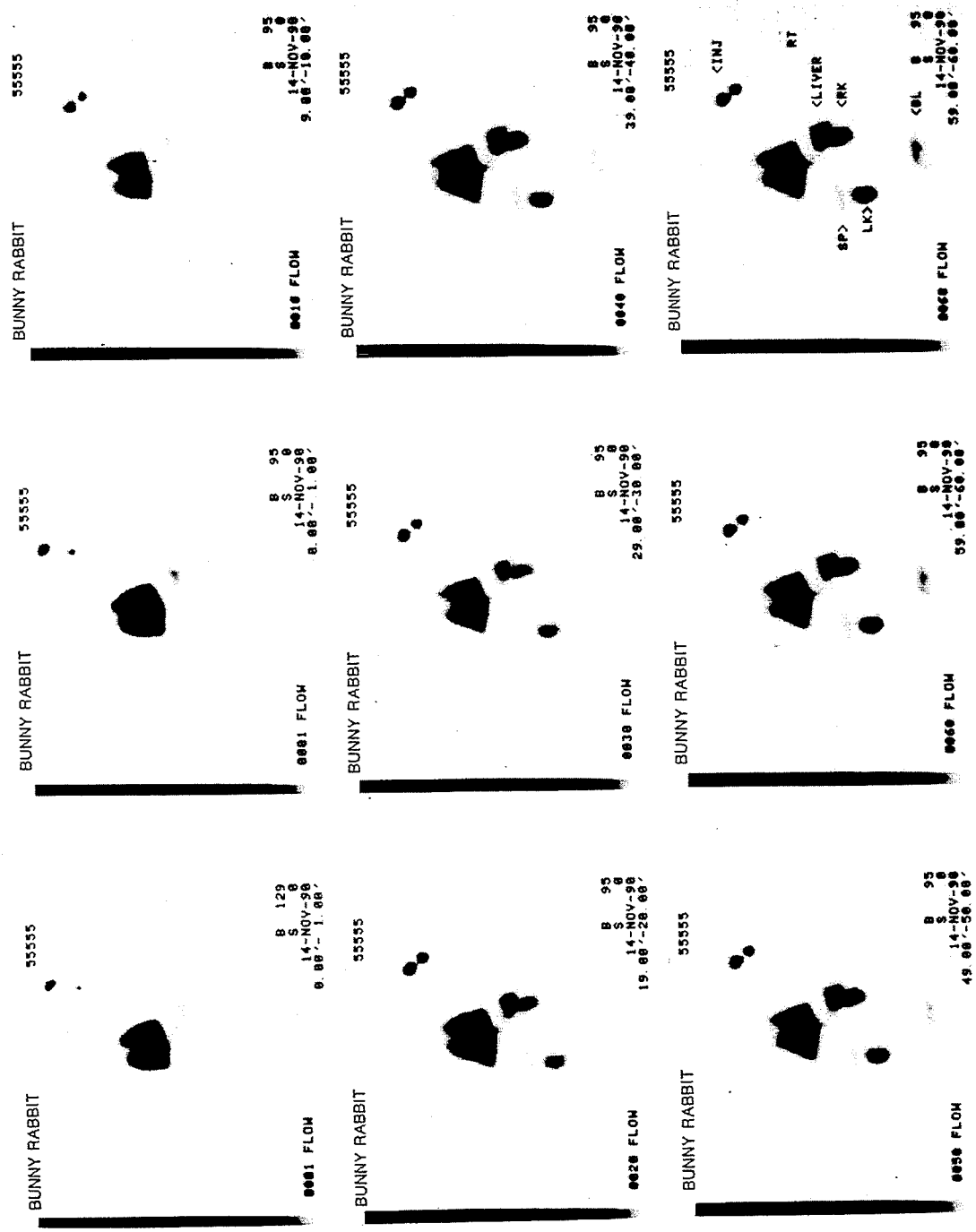
FIG. 2 shows the biodistribution of $^{99M}$technetium labeled VP6 particles in vivo. The VP6 particles are rapidly taken up by the alveolar macrophages (t=<1 min).

In one aspect, the invention is directed to methods to label macrophages and monocytes specifically in an environment which contains macrophages and/or monocytes in addition to other components. The specific labelling is effected by coupling a label to VP6 inner capsid protein from rotavirus and contacting the environment in which the macrophages and/or monocytes reside.

The choice of label depends on the nature of the environment. If macrophages and/or monocytes are to be labeled in vivo in a subject, it is generally convenient to use labels which are detectable through radiographic scanning—i.e., labels which are scintillographic. These labels are generally known in the art, and include, for example, technetium-99, indium-111, and radioisotopes of gallium. By use of suitable equipment, various iodine isotopes such as iodine-131 can also be readily detected. Methods for coupling such isotopes to proteins and other molecules are generally known in the art, and can be found in standard medical references.

Because of the availability of fiber optic technology, it is also possible to use various fluorescent labels and to localize their presence. Thus, commonly known fluorescent dyes such as fluorescein or dansyl, or the various porphyrin analogs can be employed as label.

For labeling in in vitro environments, detection is simplified, and all of the foregoing labels can also be used, as well as others less difficult to detect.

The VP6 carrier protein for use in the invention can be prepared directly from rotavirus cultures or can be prepared recombinantly.

The VP6 protein can be isolated from in vitro derived single-shelled virus particles by calcium chloride ($CaCl_2$) or lithium chloride (LiCl) treatment by standard techniques. See, e.g., Almeida et al., *J Med Virol* (1979) 4:269–277; Bican et al., *J Virol* (1982) 43:1113–1117; Gorziglia et al., *J Gen Virol* (1985) 66:1889–1900; Ready et al., *Virology* (1987) 157:189–198. Alternatively, the VP6 protein can be produced by recombinant DNA techniques. Methods for such production are described in the above-referenced U.S. Pat. No. 5,071,651.

After coupling of the label to the VP6 protein using standard technology known in the art and discussed more fully below, the resulting complex is used to contact the environment containing macrophage and/or monocytes. For in vivo administration, typically, compositions are prepared as injectables, either as liquid solutions or suspensions. The preparation may also be emulsified. The labeled VP6 complex may be mixed with excipients which are pharmaceutically acceptable and compatible with the complex. Suitable excipients are, for example, water, saline, dextrose, glycerol, ethanol, or the like, and combinations thereof. In addition, if desired, the compositions may contain minor amounts of auxiliary substances such as wetting or emulsifying agents or pH buffering agents. The compositions are conventionally administered parenterally, by injection, for example, either intravenously, subcutaneously or intramuscularly. Injectable formulations will contain an effective amount of the complex, the exact amount being readily determined by one skilled in the art. The complex can range from about 0.01% to about 95% (w/w) of the injectable composition, or even higher or lower if appropriate.

Additional formulations which are suitable for other modes of administration include suppositories, in oral formulations and nasal aerosols. For suppositories, the pharmaceutical composition will include traditional binders and carriers, such as polyalkaline glycols, or triglycerides. Such suppositories may be formed from mixtures containing the complex in the range of about 0.5% to about 10% (w/w), preferably about 1% to about 2%. Oral formulations include such normally employed excipients as, for example, pharmaceutical grades of mannitol, lactose, starch, magnesium, stearate, sodium saccharin cellulose, magnesium carbonate, and the like. These oral compositions may be taken in the form of solutions, suspensions, tablets, pills, capsules, sustained release formulations, or powders, and contain from about 10% to about 95% of the active ingredient, preferably about 25% to about 70%. Intranasal formulations for mammalian subjects will usually include vehicles that neither cause irritation to the nasal mucosa nor significantly disturb ciliary function. Diluents such as water, aqueous saline, or other known substances can be employed with the subject invention. The nasal formulations may also contain preservatives such as but not limited to chlorobutanol and benzalkonium chloride. A surfactant may be present to enhance absorption of the subject proteins by the nasal mucosa.

Furthermore, the VP6 complex may be formulated into pharmaceutical compositions in either neutral or salt forms of the VP6 carrier. If salts are used, the final preparation will typically contain less than 0.15M salt. Pharmaceutically acceptable salts include the acid addition salts (formed with the free amino groups of the VP6) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, or ferric hydroxides, and such organic bases as isopropylamine, trimethylamine, 2-ethylaminoethanol, histidine, procaine, and the like.

The formulations of the present invention may be administered in a manner compatible with the dosage formulation, and in such amounts as will be effective in labeling the macrophages or monocytes. The dosages necessary to label the resident target can be determined in view of this disclosure by one of ordinary skill in the art by running routine trials with appropriate controls. Comparison of the appropriate treatment groups to the controls will indicate whether a particular dosage is effective. In general, effective dosage will vary depending on the mode of administration. For example, in the case of an intramuscular injection, generally from 0,001 $\mu g/kg$ to 10 $\mu g/kg$ will find use in the instant invention.

After administration of the labeled complexes to the environment, the location of the macrophages and/or monocytes is determined by detecting the label. The means of detection depends on the nature of the label used; for scintillographic labels such as technetium-99 whole-body scintillography can be employed. For more weakly-emitting radiolabels or for fluorescent labels, more sensitive scanning techniques are required.

In addition to direct labeling of macrophages and/or monocytes using the natural homing abilities of the VP6 carrier, the labels described above can be directed to a selected target by formation of a tripartite complex composed of the VP6 carrier, a targeting agent, and the label. Targeting agents are those generally employed in the art for directing biological reagents specifically to target tissues and include, for example, antibodies and the immunologically reactive fragments thereof, anti-idiotypes, mimotopes, receptor ligands, or other agents which specifically bind target cells or tissues. Suitable targets include tumors, infected cells, or any other group of cells or tissues whose localization would be advantageous.

Means to couple the targeting agent to the labeled VP6 (whose preparation was described above) include direct conjugation using standard chemical techniques or advantage can be taken of the ability of VP6 to bind certain "binding peptides" through peptide-peptide interaction. The nature of the binding peptides is described in detail in the above-referenced U.S. Pat. No. 5,071,651. If a binding peptide is used, standard conjugation techniques are employed to attach the binding protein to the antibody or fragment thereof or other targeting agent. If the targeting agent is a protein, it may be prepared as a fusion protein with the binding peptide. If the targeting agent is a carbohydrate, it may be coupled directly to the VP6 carrier using standard coupling technology or may be coupled, using this technology, to the binding peptide which is in turn then linked to the VP6 carrier through protein-protein interaction. Whatever the mode of coupling, the labeled VP6 is converted to a tripartite complex containing the targeting agent.

The tripartite complexes are administered in vivo in a manner analogous to that described above for the duplex formed from VP6 and label alone.

In addition to utilizing the targeting agent coupled VP6 to deliver label to specific targets, this bipartite complex can be converted to a counterpart tripartite complex for the delivery of drugs or other effector agents. These effector agents are coupled to the bipartite complex using standard coupling techniques, including taking advantage of the protein-protein interaction with binding peptide. Since the VP6 particles can contain about 720 monomers, multiple sites for binding protein interaction or other conjugation are available.

The tripartite complexes which contain biological effectors rather than label are administered in a manner similar to that described above. Typical effector agents which can be conjugated to the VP6 include but are not limited to cytokines such as interferon (IFN) alpha, beta and gamma; colony stimulating factors such as granulocyte-macrophage CSF (CSF-GM), macrophage CSF (CSF-M), neutrophilic granulocyte CSF (CSF-G), BPA, multi-CSF, HCGF, MCGF, and PSF (see, e.g., Metcalf *Science* (1985) 229:16), primitive cell colony stimulating factor (CSF-PC), macrophage inflammatory factor, tumor necrosis factor (TNF); and interleukins such as IL-1, IL-2, IL-3, IL-4, IL-5, IL-6, IL-7, IL-8, IL-9, IL-10, IL-11 (see, e.g. *Ann Rev Immunol* Vols. 1–8).

Other effectors include additional proteins, glycoproteins, and peptides such as hormones, glucagon, insulin-like growth factors, growth hormone, thyroid stimulating hormone, prolactin, inhibin, secretin, neurotensin, cholecystokinin or fragments thereof, calcitonin, somatostatin, thymic hormones, neurotransmitters and blockers, peptide-releasing factors (e.g., enkephalins), growth hormone releasing factor, as well as fragments of proteins, such as calmodulin, *E. coli* heat stable and heat labile enterotoxin, cholera toxin; and enzymes, such as protein kinase of Rous sarcoma virus. Nucleotides useful, for instance, in oligonucleotide-based therapies include polynucleotide fragments, restriction enzyme sites, and cyclic nucleotides (e.g., cyclic adenosine monophosphate). Carbohydrates and carbohydrate complexes include bacterial capsules or exopolysaccharides (e.g., from Hemophilus influenzae B), bacterial lipid A associated core antigens (e.g., from Pseudomonas species), blood group antigens (e.g., the ABO antigens), and glycolipids. Lipids include fatty acids, glycerol derivatives, prostaglandins (e.g., prostaglandin $E_2$), and lipopeptides (e.g., leukoteiene $B_4$). Molecules of interest can also include alkaloids, such as vindo-line, serpentine, catharanthine, as well as vitamins containing —OH, NH, SH, CHO, or COOH functional groups and steroid hormones, such as testosterone, estradiol, aldosterone, endorostenedione, or fragments thereof.

A wide variety of therapeutic agents including cytotoxic agents, mutagens, antibacterial, antiviral, antifungal and antiparasitic agents will also find use in the instant invention, including but not limited to such drugs as ricin, cyclosporin A, streptomycin, amphotericin B, aflatoxin vincristine, doxorubicin, propranolol, porphyrins, acyclovir and AZT.

The use of the labeled complexes and the tripartite complexes containing effector molecules in in vitro environments is straightforward as the environment can be directly contacted with the complex and the label detected or the effect of the biological effector determined.

The following examples are intended to illustrate but not to limit the invention.

PREPARATION A

Production of Recombinant VP6

The construction of recombinant Autographa californica nuclear polyhedrosis virus (AcNPV) containing gene 6 from bovine rotavirus (BRV) and assembly of VP6 particles following infection of spodoptera frugiperda (SF9) cells is conducted as follows. Genomic RNA extracted from purified bovine rotavirus strain C486 was used to produce cDNA. The cDNA was ligated into the Pst I site of pBR322 and used to transform *E. coli* strain DH1. The resulting colonies were probed with radiolabeled cDNA prepared from purified genomic RNA segment 6 as template.

Clone pR6–42 which contained a complete copy of the gene 6 RNA, was partially digested with AhaIII which removed seven 5' noncoding nucleotides as well as the oligo-dC tails added during cDNA cloning. A BamHI linker was then added.

The 3' oligo-dC tail and noncoding region were removed by digestion with AccI which removes 56 noncoding nucleotides from the VP6 gene. A BamHI linker was then added. The gene 6 cDNA was then ligated into the BamHI site of the baculovirus transfer vector pac373. This vector was designated pAC373BRV6 (ATCC no. 40362). Integration of the rotavirus gene into the genome of *A. californica* was then carried out by homologous recombination in *S. frugidperda* (SF9) cells as outlined by Summers, M. D. and Smith, G. E., *Texas Agricultural Station Bulletin* (1987) 1555:26–27. Recombinants were identified by plaque hybridization, as described above, using radiolabeled cDNA prepared from purified genomic RNA segment 6. Recombinants were plaque purified and analyzed for expression of recombinant gene 6 produced proteins by SDS-PAGE analysis and Western blotting using the methods described above.

The recombinant virus containing gene 6 was used to infect SF9 cells. Following incubation for 72 hr at 27° C. the cells were lysed in a 2 ml NaHCO$_3$ buffer (pH 7.5) containing 0.05% triton X-100 and 0.2 trypsin inhibitor units per ml. Cellular debris was removed by centrifugation at 1500 g. The supernatant containing the recombinant VP6 protein was dialyzed against 0.1M glycine buffer (at approximately pH 2.4) for 24 hr. This dissociates VP6 aggregates into monomers. The dialysis solution was exchanged for 0.01M citrate buffer (pH 4.0) and dialysis continued for 24 hr, during which time spheres of VP6 formed. This dialysis buffer was exchanged for 0.01M citrate buffer (pH 5.0). Dialysis was then continued overnight at 4° C. Nonaggregated material was removed by ultracentrifugation using 300,000 dalton molecular weight cutoff filters. The quality of the VP6 spheres produced by this method was determined by electromicroscopy and purity confirmed by SDS-PAGE.

EXAMPLE 1

Preparation of Labeled VP6

A 0.1 ml aliquot of a solution containing 20 mg/ml of SnC12 was added to 10 ml of saline. 0.4 ml of this solution was added to 1.0 ml of the VP6 prepared as in preparation A (220 µg/ml) and then incubated for 20 min at room temperature. An aliquot of 0.2 ml of a solution of $^{99M}$technetium prepared in the standard art-recognized protocol was added and the incubation was continued for another 2 hr. An aliquot of the solution was assessed by thin-layer chromatography on silica-coated plates using saline as a solvent and showed that the radiolabel was incorporated with an efficiency of more than 85%.

EXAMPLE 2

In vitro Labeling of Macrophages

Bovine alveolar macrophages were obtained by bronchoalveolar lavage as described by Bielefeldt-Ohmann et al., *Vet Immunol Immunopathol* (1986) 13:331–346. The cells were distributed into the wells of a 96-well tissue culture plate at $5\times10^5$ cells/well. The plate was modified to allow each well to be individually separated and counted in a gamma-radiation counter. The cells were cultured overnight in Eagle's Minimal Essential Medium (MEM) containing 10% heat-inactivated horse serum.

The technetium-labeled VP6 prepared in Example 1 was added to the plate (0.2 $\mu$Ci/well) and the plate was incubated for various times. The supernatants were then removed and the cells were washed twice with MEM before counting.

FIG. 1 shows the results of this labeling as a function of time. As shown in the figure, the labeled VP6 was incorporated with about 15% efficiency after 15 min, while a control colloid preparation consisting of technetium-labeled colloidal particles of approximately the same diameter (70 nm) as the VP6 particle were not incorporated.

EXAMPLE 3

Biodistribution in vivo

A rabbit was injected intravenously with 1 mCi of technetium-labeled VP6 particles prepared as in Example 1. The distribution of label was followed over time with the results shown in FIG. 2. The complex is rapidly taken up by the alveolar macrophages in the lungs (t= <1 min). With the passage of time, label appears in the liver and kidneys. This probably represents radiolabel released from the complex as it is processed in the macrophages.

EXAMPLE 4

Colorectal Cancer Imaging

Monoclonal antibody specific for CEA is coupled to VP6 using SMCC linker. The resulting duplex is labeled with $^{99M}$technetium as described in Example 1 to produce a tripartite complex to target colorectal tumors.

We claim:

1. A method for locating macrophages and/or monocytes in an in vitro or in vivo environment comprising macrophages and/or monocytes which method comprises contacting said environment with a complex comprising a targeting agent specific for macrophages and/or monocytes wherein said targeting agent consists of rotaviral VP6 protein in the form of a particle and said targeting agent is coupled to a detectable label, and detecting the location of the label.

2. The method of claim 1 wherein the label is detectable through scintillographic means.

3. The method of claim 2 wherein the label is $^{99M}$technetium.

4. The method of claim 1 wherein said environment is a cell culture.

5. The method of claim 1 wherein the environment is a vertebrate subject and said contacting is conducted by administering said complex to said subject enterally or parenterally.

6. The method of claim 5 wherein said administering parenterally is conducted by injection.

7. A composition for locating macrophages and/or monocytes in an in vitro or in vivo environment comprising said macrophages and/or monocytes which composition comprises a complex including a targeting agent specific for macrophages and/or monocytes wherein said targeting agent consists of rotaviral VP6 protein in the form of a particle coupled to a signal-generating detectable label.

8. The composition of claim 7 wherein said detectable label is a scintillographically detectable label.

9. The composition of claim 8 wherein said label is $^{99M}$technetium.

* * * * *